(12) United States Patent
Nielsen et al.

(10) Patent No.: US 12,171,587 B2
(45) Date of Patent: Dec. 24, 2024

(54) METHOD OF ESTIMATING A HEARING LOSS, A HEARING LOSS ESTIMATION SYSTEM AND A COMPUTER READABLE MEDIUM

(71) Applicant: WIDEX A/S, Lynge (DK)

(72) Inventors: Jens Brehm Bagger Nielsen, Ballerup (DK); Asger Ougaard, Frederikssund (DK); Andreas Trier Poulsen, Hilleroed (DK)

(73) Assignee: Widex A/S, Lynge (DK)

( * ) Notice: Subject to any disclaimer, the term of this patent is extended or adjusted under 35 U.S.C. 154(b) by 245 days.

(21) Appl. No.: 17/791,264

(22) PCT Filed: Jan. 14, 2021

(86) PCT No.: PCT/EP2021/050714
§ 371 (c)(1),
(2) Date: Jul. 7, 2022

(87) PCT Pub. No.: WO2021/144373
PCT Pub. Date: Jul. 22, 2021

(65) Prior Publication Data
US 2023/0036155 A1 Feb. 2, 2023

(30) Foreign Application Priority Data
Jan. 15, 2020 (DK) .............................. PA202000050

(51) Int. Cl.
*A61B 5/00* (2006.01)
*A61B 5/12* (2006.01)
*A61B 5/38* (2021.01)
*G16H 50/30* (2018.01)

(52) U.S. Cl.
CPC .............. *A61B 5/7275* (2013.01); *A61B 5/125* (2013.01); *A61B 5/38* (2021.01); *G16H 50/30* (2018.01)

(58) Field of Classification Search
CPC ......... A61B 5/7275; A61B 5/125; A61B 5/38; G16H 50/30
USPC ........................................ 381/6, 1, 5, 4, 3, 2
See application file for complete search history.

(56) References Cited

U.S. PATENT DOCUMENTS

| | | | |
|---|---|---|---|
| 2010/0257128 A1* | 10/2010 | De Vries | G06N 20/00 703/2 |
| 2012/0070023 A1 | 3/2012 | Nishizaki | |
| 2013/0202123 A1 | 8/2013 | Nishizaki et al. | |
| 2014/0254842 A1 | 9/2014 | Smith et al. | |
| 2014/0314261 A1 | 10/2014 | Selig et al. | |
| 2017/0300631 A1 | 10/2017 | Bertrand et al. | |
| 2019/0110135 A1* | 4/2019 | Jensen | H04R 25/505 |

FOREIGN PATENT DOCUMENTS

WO    2019/195866 A1    10/2019

OTHER PUBLICATIONS

International Search Report of PCT/EP2021/050714 dated May 11, 2021 [PCT/ISA/210].
Written Opinion of PCT/EP2021/050714 dated May 11, 2021 [PCT/ISA/237].
Danish Office Action of PA202000050 dated Jul. 2, 2020.

* cited by examiner

*Primary Examiner* — Thjuan K Addy
(74) *Attorney, Agent, or Firm* — Sughrue Mion, PLLC

(57) ABSTRACT

A method of estimating a hearing loss based on a parameterized representation of a plurality of audiograms and a hearing estimation system adapted to carry out the method.

18 Claims, 2 Drawing Sheets

METHOD OF ESTIMATING A HEARING LOSS, A HEARING LOSS ESTIMATION SYSTEM AND A COMPUTER READABLE MEDIUM

CROSS REFERENCE TO RELATED APPLICATIONS

This application is a National Stage of International Application No. PCT/EP2021/050714 filed on Jan. 14, 2021, claiming priority based on Danish Patent Application No. PA202000050 filed on Jan. 15, 2020.

The present invention relates to a method of estimating a hearing loss. The invention also relates to a hearing loss estimation system. Furthermore, the invention relates to a non-transitory computer readable medium carrying instructions which, when executed by a computer, cause a hearing loss of an individual test person to be estimated.

BACKGROUND OF THE INVENTION

Generally a hearing aid system according to the invention is understood as meaning any system which provides an output signal that can be perceived as an auditory signal by a user or contributes to providing such an output signal, and which has means adapted to compensate for an individual hearing loss of the user or contribute to compensating for the hearing loss of the user. These systems may comprise hearing aids that can be worn on the body or on the head, in particular on—or in the ear, or that can be fully or partially implanted. However, a device whose main aim is not to compensate for a hearing loss, for example a consumer electronic device (televisions, hi-fi systems, mobile phones, MP3 players etc.), may also be considered a hearing aid system, provided it has measures for compensating for an individual hearing loss.

Within the present context a hearing aid can be understood as a small, battery-powered, microelectronic device designed to be worn behind or in the human ear by a hearing-impaired user. Prior to use, the hearing aid is adjusted by a hearing aid fitter according to a prescription. The prescription is based on a hearing test, resulting in a so-called audiogram, of the performance of the hearing-impaired user's unaided hearing. The prescription is developed to reach a setting where the hearing aid will alleviate a hearing loss by amplifying sound at frequencies in those parts of the audible frequency range where the user suffers a hearing deficit. A hearing aid comprises one or more microphones, a battery, a microelectronic circuit comprising a signal processor, and an acoustic output transducer. The signal processor is preferably a digital signal processor. The hearing aid is enclosed in a casing suitable for fitting behind or in a human ear.

According to variations, the hearing aid need not comprise a traditional loudspeaker as output transducer. Examples of hearing aid systems that do not comprise a traditional loudspeaker are cochlear implants, implantable middle ear hearing devices (IMEHD), bone-anchored hearing aids (BAHA) and various other electro-mechanical transducer based solutions including e.g. systems based on using a laser diode for directly inducing vibration of the eardrum.

Within the present context a hearing aid system may comprise a single hearing aid (a so called monaural hearing aid system) or comprise two hearing aids, one for each ear of the hearing aid user (a so called binaural hearing aid system). Furthermore, the hearing aid system may comprise an external device, e.g. a smart phone, having software applications adapted to interact with other devices of the hearing aid system. Thus within the present context the term "hearing aid system device" may denote a hearing aid or an external device.

In a traditional hearing aid fitting, the hearing aid user travels to an office of a hearing aid fitter, and the user's hearing aids are adjusted using the fitting equipment that the hearing aid fitter has in his office. Typically, the fitting equipment comprises a computer capable of executing the relevant hearing aid programming software and a programming device adapted to provide a link between the computer and the hearing aid.

However, it has been suggested to enable the hearing aid user to carry out at least some parts of the initial hearing aid fitting or a subsequent fine-tuning. One such part could e.g. be the recording of the user's frequency dependent hearing loss threshold, that in the following may also be denoted an audiogram.

The hearing loss of a hearing-impaired person is generally frequency-dependent and may not be the same for both ears. This means that the hearing loss of the person varies depending on the frequency. Therefore, when compensating for hearing losses, it can be advantageous to utilize frequency-dependent amplification. Hearing aids therefore often provide band split filters in order to split an input sound signal received by an input transducer of the hearing aid, into various frequency intervals, also called frequency bands, which are independently processed. In this way it is possible to adjust the input sound signal of each frequency band individually to account for the hearing loss in respective frequency bands. The frequency dependent adjustment is normally done by implementing a band split filter and a compressor for each of the frequency bands, hereby forming so-called band split compressors, which may be combined to form a multi-band compressor. In this way it is possible to adjust the gain individually in each frequency band depending on the hearing loss as well as the input level of the input sound signal in a respective frequency band. For example, a band split compressor may provide a higher gain for a soft sound than for a loud sound in each frequency band.

Traditionally a hearing aid system is fitted-initially or as part of a subsequent fine tuning-based primarily or exclusively on a recorded audiogram for the individual haring aid system user.

Generally hearing screening or hearing test methods that allow the hearing loss of an individual to be tested are well known in the art.

Perhaps the most widespread method is based on pure tone tests, where the individual to be tested (i.e. the test person) is presented for a tone at a specific frequency and at first at a very low loudness that most probably is not audible for the test person, where after the loudness is progressively increased until the test person indicates that the tone is audible whereby the hearing threshold may be established, and from that the hearing loss at that specific frequency as compared to normal hearing subjects may be derived. In order to fully characterize the hearing loss the test may be repeated for other frequencies in the audible range.

This type of test has been offered as online test for many years. Hereby individuals that suspect they may have a hearing loss can take the test at home and record their audiogram without having to make an appointment and travel to a hearing care professional.

However, this type of test may be time consuming and some users consider the test uncomfortable and annoying, which additionally may lead to a recorded audiogram of low accuracy. Furthermore, a hearing care professional will obviously also benefit from a less time consuming and less uncomfortable (for the hearing impaired) hearing test.

It is therefore a feature of the present invention to provide an improved method of estimating a hearing loss.

It is another feature of the present invention to provide a hearing loss estimation that is simple to carry out for the test person.

It is still another feature of the present invention to provide a hearing loss estimation that may be carried out by the test person in a very short time.

It is yet another feature of the present invention to provide a hearing loss estimation that may provide improved test results at least for some users as a result of at least one of the short duration of the test and as a result of the specific frequencies selected to measure a hearing threshold.

SUMMARY OF THE INVENTION

The invention, in a first aspect, provides a method of estimating a hearing loss according to claim 1.

This provides an improved method of estimating a hearing loss.

The invention, in a second aspect, provides a hearing estimation system according to claim 6.

This provides an improved hearing estimation system.

Further advantageous features appear from the dependent claims.

Still other features of the present invention will become apparent to those skilled in the art from the following description wherein the invention will be explained in greater detail.

BRIEF DESCRIPTION OF THE DRAWINGS

By way of example, there is shown and described a preferred embodiment of this invention. As will be realized, the invention is capable of other embodiments, and its several details are capable of modification in various, obvious aspects all without departing from the invention. Accordingly, the drawings and descriptions will be regarded as illustrative in nature and not as restrictive. In the drawings.

DETAILED DESCRIPTION

Within the present context the terms frequency dependent hearing threshold, audiogram and frequency dependent threshold of hearing curve may be used interchangeably, despite that an audiogram according to a strict interpretation is not a curve nor a continuous function but only provides the audible thresholds for some standardized frequencies. Thus, typically an audiogram is given as a vector.

In the following a given frequency for which a (frequency dependent) hearing threshold is measured may also be denoted test frequency and audiogram frequency and unless otherwise noted these terms may be used interchangeably.

Within the present context the term software application may be construed to comprise a program storage for storing an executable program, and a processor for executing said program. However, the term software application may also be construed to mean a non-transitory computer readable medium carrying instructions that may be executed by a computer.

Within the present context it is understood that the value of any parameter may be denoted either simply by the name of the parameter or as the magnitude or value of the parameter.

The inventors have found, by analyzing a substantial number of audiograms from real world hearing aid users, that audiograms appear not to form distinct clusters but rather tend to exist continuously spread out over the parameter space. A consequence hereof is that most audiograms will not be similar to one of a limited number of standard audiograms-such as in the order of say 10 standard audiograms.

It is a well known issue that most hearing aid fitting systems are configured to be based on audiograms measured at say 10 or more frequencies, while the number of frequencies that have actually been measured for the audiogram may be significantly lower, such as say 4. This may be due to the limited amount of time available for a hearing aid fitter to spend on each patient or the limited amount of time the hearing aid system user is willing to spend on carrying out frequency dependent hearing threshold measurements himor herself because these may be considered cumbersome, tiring or even uncomfortable.

The present invention is therefore according to one aspect directed at reducing the number of hearing threshold measurements required to obtain an audiogram that enables a sufficiently accurate hearing aid fitting to be carried out or simply enables that the time spend on carrying out the measurements is minimized.

Furthermore, as already noted above, it may be that an audiogram in not always carried out for all prescribed frequencies.

The present invention is therefore also directed at suggesting which first and subsequent frequencies to measure hearing thresholds at in order to obtain the best possible audiogram estimation.

Figure 1:
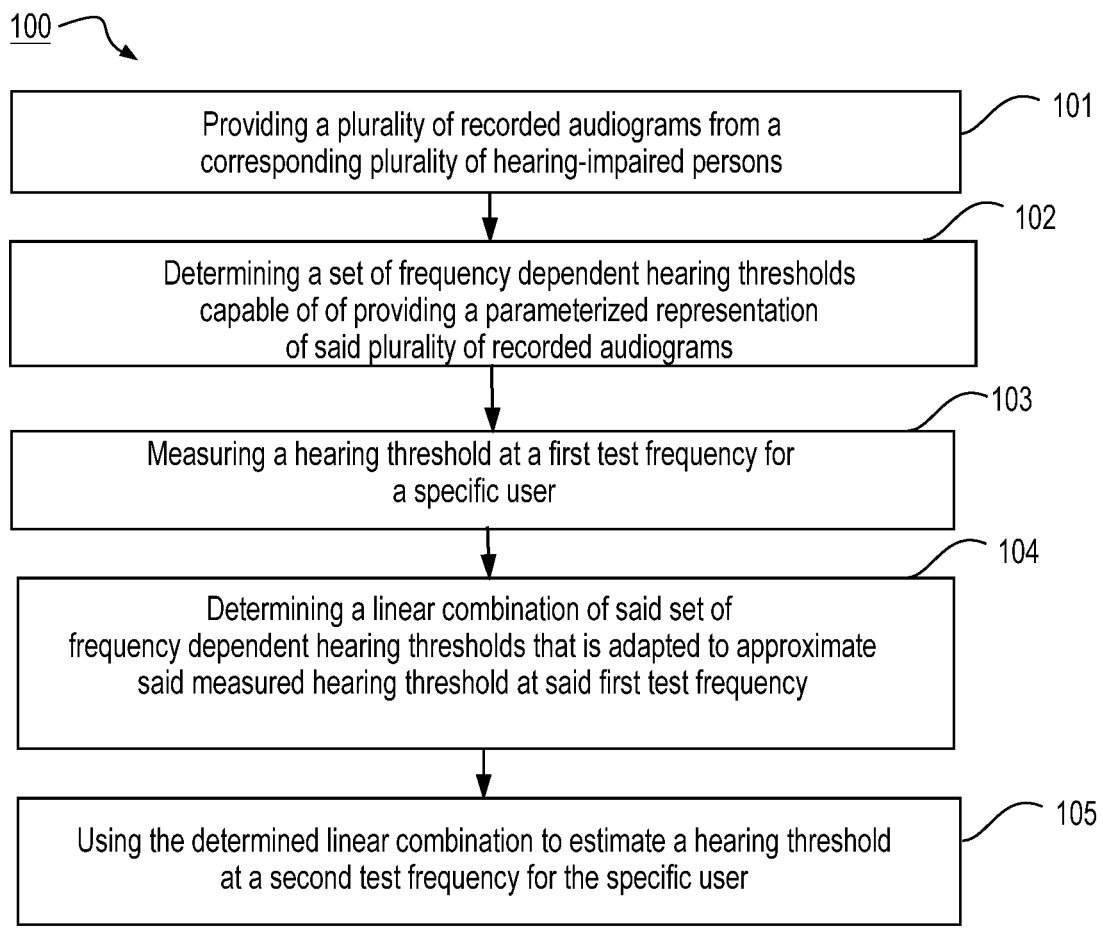
FIG. 1 illustrates highly schematically a method of estimating a hearing loss according to a first embodiment of the invention.

Reference is first made to FIG. 1 which illustrates highly schematically a method 100 of estimating a hearing loss according to a first embodiment of the invention.

In a first step 101 a first plurality N of recorded audiograms (i.e. frequency dependent hearing thresholds) is provided from a corresponding plurality of hearing-impaired persons.

In the following each audiogram is expressed as a vector x containing the hearing threshold values measured at d selected test frequencies:

$$x = [x_1, \ldots, x_d]^T$$

Thus, in the following the d-dimensional vector x with specific hearing threshold values for the d selected test frequencies may also be denoted an audiogram.

In a second step 102 a set of frequency dependent hearing thresholds providing a parameterized representation of said first plurality N of frequency dependent hearing thresholds is determined.

According to the present embodiment said set of frequency dependent hearing thresholds is determined as a second plurality P of d-dimensional archetype vectors z that are determined as the set of vectors $z_1, \ldots, z_p$ that minimizes the expression:

$$\sum_i \left\| x_i - \sum_{k=1}^{p} \alpha_{ik} z_k \right\|^2$$

under the constraints that:

$$\alpha_{ik} \geq 0 \text{ and } \sum_k \alpha_{ik} = 1$$

wherein $a_{ik}$, k=1, . . . ,p is determined as the minimizers of:

$$\left\| x_i - \sum_{k=1}^p \alpha_{ik} z_k \right\|^2$$

and wherein further the vectors $z_1, \ldots, z_p$ are given as:

$$z_k = \sum_k \beta_{jk} x_k$$

under the constraints that:

$$\beta_{ik} \geq 0 \text{ and } \sum_k \beta_{ik} = 1$$

In a third step 103 a hearing threshold is measured at a first test frequency for a specific user (i.e. the user for which the audiogram is to be estimated).

Subsequently in a fourth step 104 a linear combination of said set of frequency dependent hearing thresholds (i.e. the second plurality of archetypal vectors $z_1, \ldots, z_p$) is determined that is adapted to approximate said measured hearing threshold at said first test frequency.

In a final step 105 the determined linear combination is used to estimate a frequency dependent hearing threshold at a second test frequency for the specific user.

Hereby the determined linear combination provides an improved method of representing a large amount of audiogram data in a compressed manner.

According to a variation of the present embodiment the determined linear combination is adapted to approximate more than one hearing threshold measured at a given test frequency for a specific user. According to a further variation the test frequencies of said more than one measured hearing thresholds are selected in order to improve the expected accuracy of the determined linear combinations ability to estimate at least one hearing threshold for said specific user.

According to another variation the determined linear combination may be used to estimate more than one hearing threshold for a given test frequency.

According to a more specific embodiment the step of measuring a hearing threshold at a first test frequency (i.e. step 103) comprises the further step of selecting as said first test frequency the frequency for which a measure of the variability of the hearing thresholds for said set of archetype vectors (i.e. the set of frequency dependent hearing thresholds) is maximum. According to a more specific embodiment the measure of the variability may be selected from a group comprising: variance and standard deviation.

According to other less preferred embodiments the set of frequency dependent hearing thresholds does not consist of archetype vectors but is instead replaced by vectors determined using methods from a group comprising: principal component analysis and sparse coding.

Figure 2:
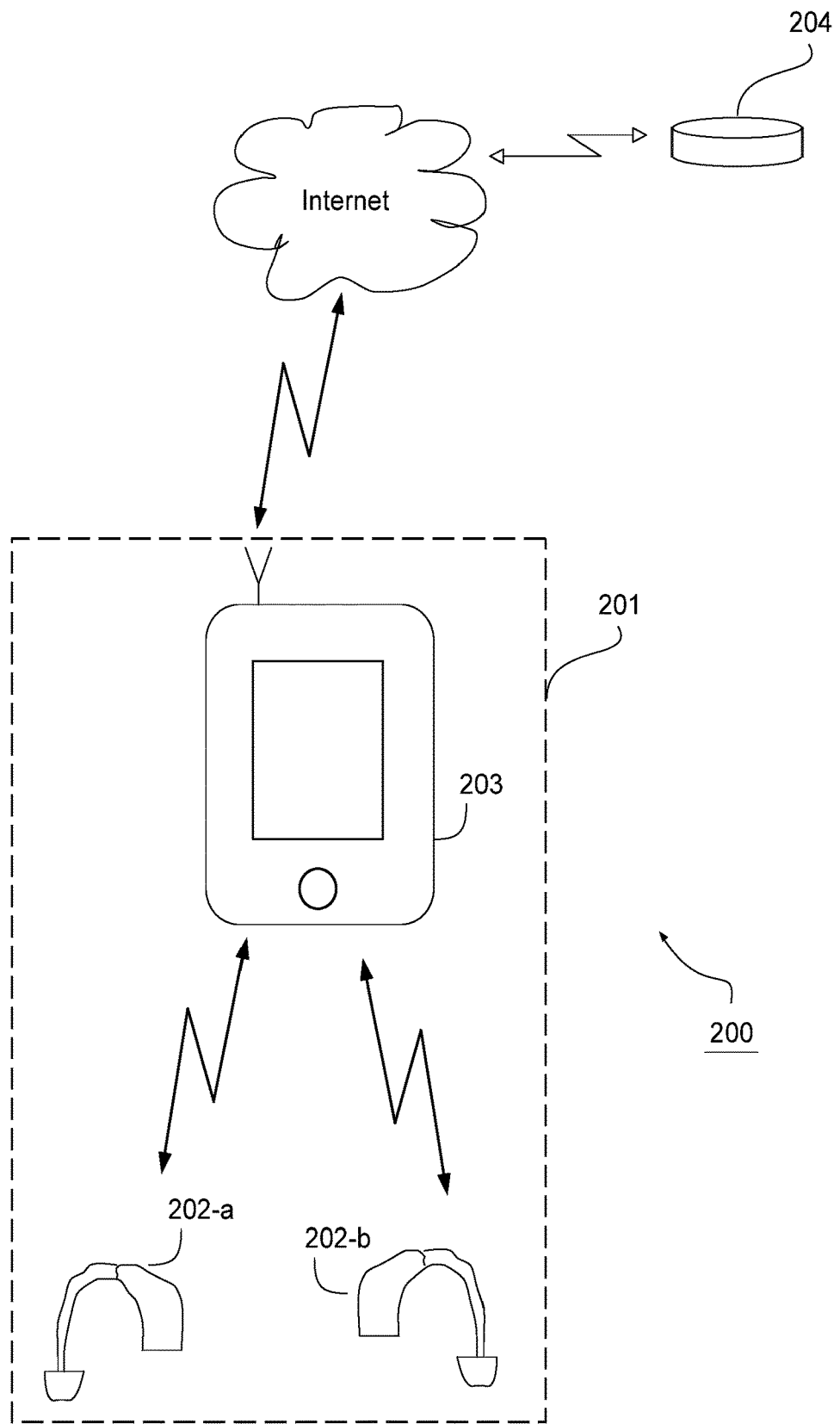
FIG. 2 illustrates highly schematically a hearing estimation system according to a second embodiment of the invention.

Reference is now made to FIG. 2, which illustrates highly schematically a hearing estimation system 200 according to a second embodiment of the invention.

The hearing estimation system 200 comprises a hearing aid system 201 consisting of a left hearing aid 202-a and a right hearing aid 202-b and an external device, in the form of a smart phone 203 with a specific software application installed.

The hearing estimation system 200 further comprises an internet server 204 that holds a first plurality of audiograms (i.e. first plurality of frequency dependent hearing thresholds) from a corresponding plurality of hearing-impaired persons.

Furthermore, the internet server 204 is adapted to determine a set of vectors suitable for providing a parameterized representation of said first plurality of audiograms According to a specific variation the set of vectors is a set of archetype vectors.

Additionally, the internet server 204 is adapted to receive from the hearing aid system 201 at least one hearing threshold measured at a first test frequency for a specific user of said hearing aid system and based hereon determine a linear combination of said set of vectors that is adapted to approximate at least said measured hearing threshold at said first frequency for said specific user.

Finally, the internet server 204 is adapted to use the determined linear combination to estimate at least one hearing threshold for at least one test frequency for the specific user and transmit said at least one estimated hearing threshold for said tested frequencies to the hearing aid system 201. Hereby an estimated audiogram may be transmitted back to the hearing aid system.

According to various embodiments at least one of the hearing aids 202-a and 202-b and the external device 203 of the hearing aid system 201 is connected directly to the internet server using a wireless link to the internet, based on e.g. the 3G, 4G or upcoming 5G broadband cellular network technology. Alternatively, the external device 203 (e.g. in the form of a smart phone) of the hearing aid system 201 may be used as gateway for the hearing aids, all of which will be well known for the skilled person.

In obvious variations the hearing aid system may consist of a single hearing aid (a so called monaural fitting) or may consist of both a left and a right hearing aid (a so called binaural fitting) and furthermore the hearing aid system may (or may not) include an external device 203.

According to a more specific embodiment the external device 203 comprises a software application and a graphical user interface configured to enable a hearing aid system user to interact with the hearing aids 202-a and 202-b such that the hearing aids 202-a and 202-b can be used to provide a desired acoustical test signal at various sound pressure levels and hereby allow the external device 203 to measure at least one hearing threshold measured at a given test frequency for the specific hearing aid system user.

According to yet another embodiment the specific software application installed on the external device 203 is replaced by a web service, that is hosted on an external server and may be accessed using e.g. a web browser of external device 203.

In further variations of the FIG. 2 embodiment the external device 203 may be a smart phone, a tablet computer, a portable personal computer or a stationary personal computer.

According to still another variation of the FIG. 2 embodiments the software application is set up to provide an acoustical test signal that is selectively provided to either the left ear or the right ear using a set of standard headphones or earphones connected to the computerized device.

It is emphasized that the hearing estimation method according to the present invention is advantageous independent on whether the hearing test is carried out as part of an initial hearing aid fitting or as part of a hearing aid fine tuning and independent on whether the hearing aid test is carried out by a hearing care professional or by the hearing aid system user.

Thus, according to one specific embodiment the hearing estimation system does not include a hearing aid system. An example of such a system is a traditional audiometer being configured to carry out the method according to the invention.

In further variations the hearing estimation systems according to the present invention may also be systems and devices that are not exclusively hearing estimation systems, i.e. they may be comprised in more generic devices such as a smart phone or various other parts of tablet computers.

In still other variations the invention is embodied as a non-transitory computer readable medium carrying instructions which when executed by a computer, cause the methods of the disclosed embodiments to be performed.

Other modifications and variations of the structures and procedures will be evident to those skilled in the art.

The invention claimed is:

1. A method of estimating a hearing loss comprising the steps of:
    providing a first plurality of audiograms from a corresponding plurality of hearing impaired persons;
    determining a set of vectors suitable for providing a parameterized representation of said first plurality of audiograms;
    measuring a first hearing threshold at a first test frequency for a specific user;
    determining a linear combination of said set of vectors that is adapted to approximate at least said measured first hearing threshold at said first test frequency; and
    using said linear combination to estimate at least one hearing threshold at a second test frequency for the specific user.

2. The method according to claim 1, wherein the step of determining a set of vectors suitable for providing a parameterized representation of the first plurality of audiograms comprises the further step of:
    using archetypal analysis of the data of the first plurality of audiograms in order to determine a set of archetype vectors that characterize said data such that each audiogram can be expressed as a combination of said set of archetype vectors and using said set of archetype vectors as said set of vectors.

3. The method according to claim 1, wherein the step of measuring a hearing threshold at a first test frequency for a specific user comprises the further step of:
    selecting as said first test frequency the frequency for which a measure of the variability of the hearing thresholds for said set of vectors is maximum.

4. The method according to claim 2, wherein the step of measuring a hearing threshold at a first test frequency for a specific user comprises the further step of:
    selecting as said first test frequency the frequency for which a measure of the variability of the hearing thresholds for said set of vectors is maximum.

5. The method according to claim 1, comprising the further step of measuring a first plurality of hearing thresholds at a corresponding first plurality of test frequencies for a specific user.

6. The method according to claim 1, wherein said second test frequency has not been measured for the specific user.

7. A hearing estimation system comprising a computerized device, an internet server and an electro-acoustical transducer, wherein the computerized device is operationally connected to both the internet server and the electro-acoustical transducer and wherein the computerized device comprises a graphical user interface, a program storage for storing an executable program and a processor for executing said program to perform the method according to claim 1.

8. The hearing estimation system according to claim 7, wherein the computerized device is a smart phone, tablet computer, portable personal computer, a stationary personal computer or an audiometer.

9. The hearing estimation system according to claim 7, wherein the step of determining a set of vectors suitable for providing a parameterized representation of the first plurality of audiograms comprises the further step of:
    using archetypal analysis of the data of the first plurality of audiograms in order to determine a set of archetype vectors that characterize said data such that each audiogram can be expressed as a combination of said set of archetype vectors and using said set of archetype vectors as said set of vectors.

10. The hearing estimation system according to claim 7, wherein the step of measuring a hearing threshold at a first test frequency for a specific user comprises the further step of:
    selecting as said first test frequency the frequency for which a measure of the variability of the hearing thresholds for said set of vectors is maximum.

11. The hearing estimation system according to claim 9, wherein the step of measuring a hearing threshold at a first test frequency for a specific user comprises the further step of:
    selecting as said first test frequency the frequency for which a measure of the variability of the hearing thresholds for said set of vectors is maximum.

12. A non-transitory computer readable medium carrying instructions which, when executed by a computer causes a method according to claim 1 to be performed.

13. The non-transitory computer readable medium according to claim 12, wherein a software application is adapted to be downloaded from an external server and subsequently may be executed independently of the external server.

14. The non-transitory computer readable medium according to claim 12, wherein a software application is adapted to be executed at least partly from an external server and adapted to be accessed using a web browser of the computer.

15. The non-transitory computer readable medium according to claim 12 wherein the step of determining a set of vectors suitable for providing a parameterized representation of the first plurality of audiograms comprises the further step of:
    using archetypal analysis of the data of the first plurality of audiograms in order to determine a set of archetype vectors that characterize said data such that each audiogram can be expressed as a combination of said set of archetype vectors and using said set of archetype vectors as said set of vectors.

16. The non-transitory computer readable medium according to claim 12 wherein the step of measuring a hearing threshold at a first test frequency for a specific user comprises the further step of:
    selecting as said first test frequency the frequency for which a measure of the variability of the hearing thresholds for said set of vectors is maximum.

17. The non-transitory computer readable medium according to claim 15 wherein the step of measuring a hearing threshold at a first test frequency for a specific user comprises the further step of:

selecting as said first test frequency the frequency for which a measure of the variability of the hearing thresholds for said set of vectors is maximum.

18. The method according to claim 1, wherein each of said vectors contains hearing threshold values measured at selected test frequencies.

\* \* \* \* \*